United States Patent [19]

Southgate

[11] 4,282,510
[45] Aug. 4, 1981

[54] APPARATUS FOR DISCERNING THE NOTICEABLE PRESENCE OF SPATIAL FLUCTUATIONS OF INTENSITY WITHIN A TWO-DIMENSIONAL VISUAL FIELD

[75] Inventor: Peter D. Southgate, Princeton, N.J.

[73] Assignee: RCA Corporation, New York, N.Y.

[21] Appl. No.: 110,244

[22] Filed: Jan. 7, 1980

[51] Int. Cl.³ ............................................. G06K 9/00
[52] U.S. Cl. ............................. 340/146.3 F; 250/572;
340/146.3 Q; 350/162 SF; 356/430; 358/106
[58] Field of Search ............... 364/515, 517, 555, 572;
340/146.3 F, 146.3 P, 146.3 Q, 146.3 AQ;
356/387, 430; 250/563, 572; 350/162 SF, 162
ZP; 358/101, 106, 107

[56] References Cited

U.S. PATENT DOCUMENTS

| 3,783,296 | 1/1974 | Blevins | 250/572 |
| 3,955,095 | 5/1976 | Gadbois et al. | 250/572 |
| 3,989,387 | 11/1976 | Hategan | 250/572 |
| 4,000,949 | 1/1977 | Watkins | 350/162 SF |
| 4,083,627 | 4/1978 | Okano | 350/162 SF |
| 4,159,164 | 6/1979 | Dammann et al. | 350/162 SF |
| 4,226,538 | 10/1980 | Van Beeck | 250/572 |

Primary Examiner—Leo H. Boudreau
Attorney, Agent, or Firm—Samuel Cohen; George J. Seligsohn

[57] ABSTRACT

System for the analysis of an optically sensed field, useful, for example, for detecting defects in an object such as a shadow mask of a color kinescope, which permits relatively rapid examination of the article or surface being scanned. An important feature of the system is a detector linear array disposed a selected distance from the image plane of the spatial field permits higher speed sequential convolution of the spatial field at each of a plurality of overlapping segments of given length, situated at uniformly-spaced intervals along a field dimension, with a given type of limited spatial extent kernel function of said given length.

19 Claims, 12 Drawing Figures

MASK SCAN DIRECTION

PERPENDICULAR TO LINEAR ARRAY PLANE

APPARATUS FOR DISCERNING THE NOTICEABLE PRESENCE OF SPATIAL FLUCTUATIONS OF INTENSITY WITHIN A TWO-DIMENSIONAL VISUAL FIELD

This application is related to the application of Peter David Southgate et al, Ser. No. 110,243 (RCA 73,388), filed on even date herewith and assigned to the same assignee as the present application.

This invention relates to improved techniques for examining a two-dimensional spatial field of intensities, such as a two-dimensional visual field, for a noticeable presence of intensity fluctuations. These improved techniques permit a much quicker examination of such a spatial field than the techniques disclosed in the aforesaid related application Ser. No. 110,243 (RCA 73,388).

Both the present invention and the one of the aforesaid related application Ser. No. 110,243 (RCA 73,388) provide quantitative techniques capable of discerning the presence of non-uniformities which are noticeable to the human eye in an otherwise uniform two-dimensional spatial field. In addition, other types of non-uniformity can be detected which may have special significance even though they may not be visible to the eye.

More particularly, as disclosed in the aforesaid patent application Ser. No. 110,243 (RCA 73,388), a section along a certain dimension of all or part of a two-dimensional spatial field of intensities is divided at uniformly-spaced intervals into a plurality of overlapping segments, each of a given length. A section is relatively long, being equal to more than one wavelength of the lower limit spatial frequency of a predetermined limited spatial frequency band. The respective segments of a section of the spatial field are sequentially convolved with a given kernel function, to give a transform function. This given kernel function is characterized by (1) having a limited spatial extent along the certain field dimension which is substantially equal to the given length of a segment, (2) having an integrated value over its limited spatial extents substantially equal to zero and (3) exhibiting a spatial frequency passband no greater than the predetermined limited spatial frequency band. An output signal, indicative of the noticeable presence of spatial non-uniformities is then derived only if the value of the q'th root of the sum of the q'th power of each of the respective convolutions is at least equal to a predetermined threshold value (where q is a given-valued number and where the predetermined threshold value corresponds with a just-noticeable presence of non-uniformities having dominant spatial frequencies within the kernel function spatial frequency band).

For illustrative purposes, this related application discloses an inspection system for discerning noticeable non-uniformities in the two-dimensional visual field of a manufactured object (i.e., a shadow mask for a color picture tube). This related application discloses one embodiment employing electronic processing means, in which sampled detected data values, derived from a shadow mask scanned past a small viewing aperture, are sequentially convolved at each of a plurality of uniformly-spaced intervals with a given kernel function, to produce a series of values of the transform function. This one embodiment requires a very large number of processing steps in order to discern all the non-uniformities of interest which may be present in the inspected shadow mask. This related application also discloses other embodiments employing optical processing means for accomplishing the aforesaid sequential convolutions. While these optically-convolving embodiments require substantially fewer processing steps than does the electronically-convolving embodiment, the required number of processing steps in still very large.

The present invention is directed to various techniques for significantly reducing the number of separate signal processing steps required for sequentially convolving uniformly-spaced segments of a spatial two-dimensional field of intensities. In accordance with the principles of the present invention, the sequential convolving of the spatial two-dimensional field with a given kernel function having the aforesaid characteristics is performed by signal processing means including detector means comprising a linear array of contiguous detector elements, optical processing means and electronic processing means. More specifically, the linear array is oriented along a given line of a given plane perpendicular to the optic axis of the system, while the optical processing meeans images an illuminated object (from which the spatial two-dimensional field is derived) on an image plane that is displaced a selected fixed distance from the given plane of the linear array. Because the linear array is displaced a selected fixed distance from the image plane, each detector element thereof is simultaneously illuminated by an extended region of the two-dimensional spatial field derived from the scanning object. The respective extended regions corresponding to adjacent detector elements of the array overlap. It will now be shown how this arrangement may be exploited so that the detector array output is a transform of the visual field.

Figure 1:
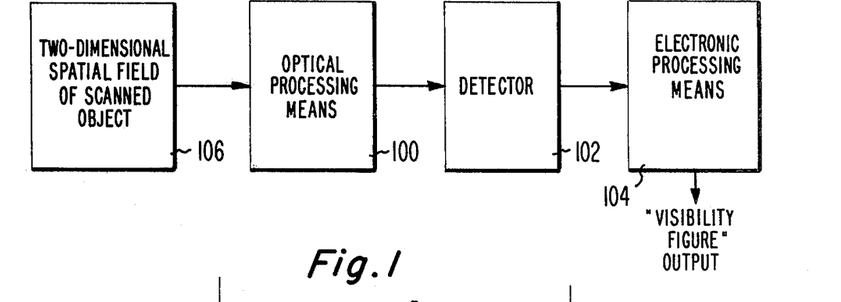
FIG. 1 is a functional block diagram of the type of apparatus with which both the present invention and the invention disclosed in the aforesaid related patent application Ser. No. 110,243 (RCA 73,388) are concerned.

Referring to FIG. 1, there is shown a functional block diagram of signal processing means for deriving an output indicative of certain spatial frequency pattern characteristics of a two-dimensional spatial field of intensities derived from a scanned object, such as a shadow mask of a color picture tube. Specifically, the signal processing means includes optical processing means 100, detector means 102 and electronic processing means 104. Block 106 includes means for producing a two-dimensional spatial field of intensities from an illuminated scanned object. The spatial field may contain both patterns of no interest and patterns of interest. For instance, in the case of an inspection system for a shadow mask, the uniform high spatial-frequency pattern formed by the regular of a shadow mask apertures is of no interest, and must be filtered out before detection. However, patterns of lower spatial frequencies, caused by defects in the shadow mask, are of interest since they are subjectively noticeable. Therefore, optical processing means 100 filters out spatial frequencies higher than the highest spatial frequency of interest before detection by detector means 102. In those cases where the required sequential convolving (discussed above) is accomplishd optically, optical processing means 100 includes the required convolution means. However, in those cases where the required convolution is accomplished electronically, electronic processing means 104 includes the required convolution means. Further, electronic processing means 104 may include sampling means, memory means, and a convolution output combiner and threshold comparator means, which are more fully disclosed in the aforesaid related patent application Ser. No. 110,243 (RCA 73,388).

Briefly, such combiner and threshold comparator means performs the function of computing the value of the q'th root of the sum of the q'th power of a series of a predetermined number of successive convolution outputs (where q is a predetermined plural integer such as 4). Then, only if this computed value is greater than a threshold value corresponding to the just-noticeable presence of non-uniformities within the passband of the convolution kernel function then being used, is an output signal produced. In the case of a shadow mask, each of a plurality of different spatial sections is examined with a plurality of separate convolution kernel functions that have different center-frequency values (each of which values has its own threshold value corresponding thereto). The shadow mask is rejected when the defects thereof, as evidenced by the respective values of the combiner output signals for each of these different certain sections and separate center-frequencies, exceeds a certain criterion. Reference should be made to the aforesaid related patent application Ser. No. 110,243 (RCA 73,388) for a more detailed description of a scanned shadow mask inspection system. However, in general, the output of electronic processing means 104 is indicative of the degree to which the intensity non-uniformities in the spatial field of the scanned object will be subjectively observable.

Figure 2:
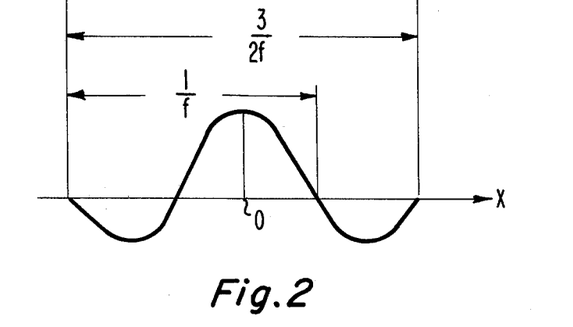
FIG. 2 is a graph of a given kernel function suitable for use in the apparatus in FIG. 1.

A limited spatial extent kernel function, which exhibits a spatial passband of substantially one octave, is the waveform $\cos(2\pi fx) \cos(2\pi fx/3)$ shown in FIG. 2. As shown in FIG. 2, the spatial extent of this kernel function is 3/2 wavelengths long. If f is the mid-frequency of an octave, the passband of the octave extends from $\frac{2}{3}f$ to $4/3f$ (i.e., the upper frequency of the passband is twice the lower frequency of the passband). By employing a plurality of such kernel functions; in which the respective values of f are chosen to be in geometric progression, a predetermined limited spatial frequency band having a bandwidth equal to the sum of the individual band-widths can be realized. Although the particular kernel function having the waveform shown in FIG. 2 is a preferred kernel function employed in describing the present invention, it should be understood that the present invention contemplates the use of any type of kernel function that is characterized by (1) having a limited spatial extent along a certain dimension of a two-dimensional spatial field of intensities, (2) having an integrated value over its limited spatial extent substantially equal to zero and (3) exhibiting a limited spatial frequency passband.

Figure 3A:
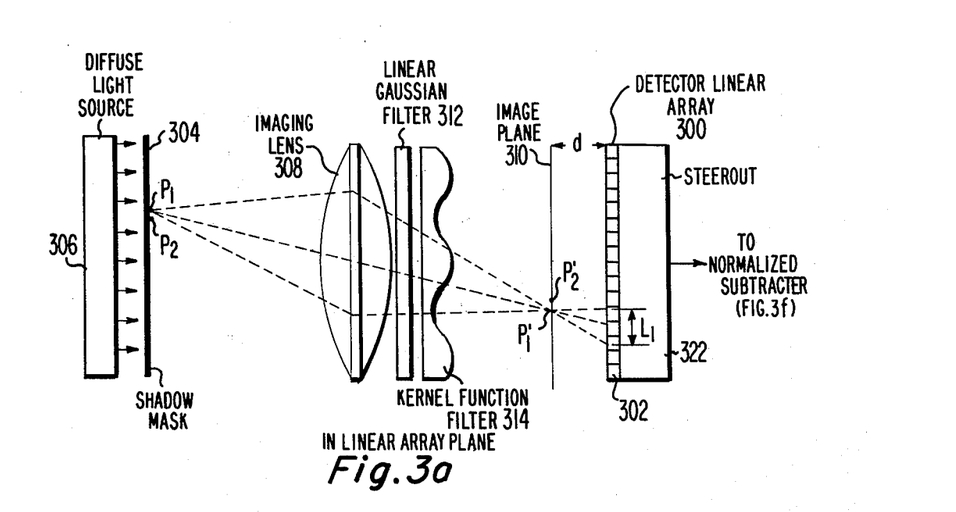
FIGS. 3a, 3b, 3c, 3d and 3e illustrate a first embodiment of the present invention.
Figure 3B:
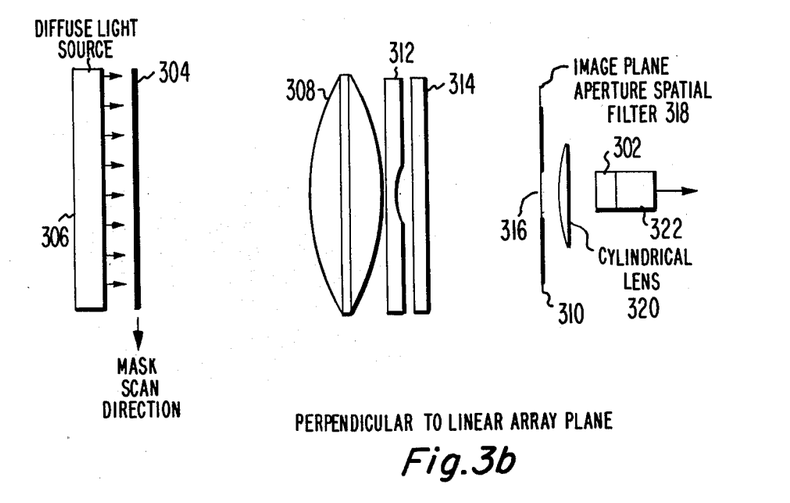

Reference is made to FIGS. 3a and 3b, which illustrate a first embodiment (of the two-dimensional spatial field of scanned object 106, optical processing means 100 and detector means 102 of FIG. 1) which incorporates the principles of the present invention. Specifically, detector means 102 comprises detector linear array 300 composed of a plurality of contiguous detector elements 302 orineted along a given line of the given plane shown in FIG. 3a. As shown in FIG. 3b, the length of each detector element 302 in a plane perpendicular to the linear array plane of FIG. 3a is substantially larger than the width of each detector element 302 in the linear array plane of FIG. 3a.

The plurality of detector elements 302 of detector linear array 300 are illuminated by optically-processed light passed through the respective apertures of the shadow mask 304, mechanically scanned in a scan direction perpendicular to detector linear array 300. The mechanical scan may be stepwise or continuous. Shadow mask 304 is illuminated from behind by diffuse light source 306. The light transmitted through shadow mask 304 comprises a two-dimensional spatial field of light intensities. This spatial field includes a substantially uniform high spatial-frequency pattern due to the regular array of closely-spaced shadow-mask apertures. However, this spatial field may also include non-uniform patterns of lower spatial frequencies due to defects in shadow mask 304. By way of example, these defects may include partly or wholly blocked individual apertures, small tears in the mask, or apertures of unequal size over the area of the mask.

The two-dimensional spatial light field emerging from shadow mask 304 is imaged by imaging lens 308 on an image plane 310 situated a selected distance d in front of the given plane occupied by detector linear array 300. However, situated in proximity to imaging lens 308, in the path of the two-dimensional spatial field light being imaged, are both linear Gaussian filter 312 and linear kernel function filter 314. The term "linear" here indicates a filter whose density varies in one direction in its plane but not in an orthogonal directin in its plane. This orthogonal direction is called the "axis" of the filter. As indicated in FIGS. 3a and 3b, Gaussian filter 312 provides a Gaussian characteristic in the plane of FIG. 3b (perpendicular to the linear array direction). Kernel function filter 314 is also a linear filter, but, has its axis nearly, but not exactly, perpendicular to the direction of the linear array.

Further, as shown in FIG. 3b, the detector elements 302 of detector linear array 300 are illuminated by only that portion of the imaged light passing through viewing aperture 316 of image plane aperture spatial filter 318, shown in FIG. 3b. In order to effectively increase the length of the detector elements 302, and thereby maximize the amoung of light flux passing through viewing aperture 316 which impinges on the detector elements 302 of detector linear array 300, cylindrical lens 320 is disposed between viewing aperture 316 and detector elements 302 of detector linear array 300, as shown in FIG. 3b.

Associated with detector linear array 300 (but really forming part of electronic processing means 104) is steerout means 322, shown in FIGS. 3a and 3b. The output from steerout means 322 is applied as an input to a normalized subtractor portion of the electronic processing means, shown in FIG. 3f (discussed below).

Detector linear array 300 is of the type in which each detector element 302 accumulates a stored photoelectric charge proportional to the total light exposure thereof between successive electronic scans of array 300 by steerout means 322. In practice, a vidicon may comprise array 300 together with steerout means 322. Preferably, however, array 300 is comprised of solid-state photoelectric detector elements 302.

Linear Gaussian filter 312 may be a graded transmission filter, in which the light-absorption density varies spatially in accordance with the desired linear Gaussian characteristics. Kernel function filter 314 may also be in the form of a graded transmission filter, or it may be a variable intermittancy filter of the form shown in FIG. 3c.

Figure 3C:
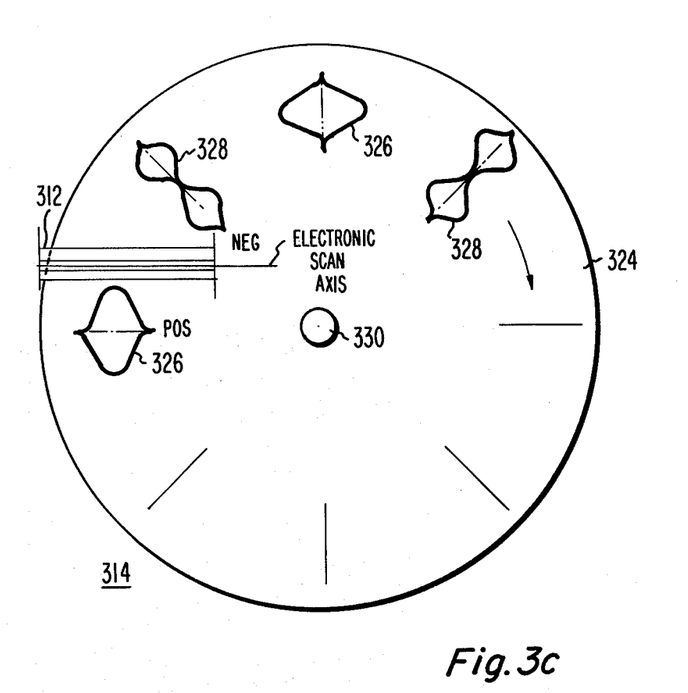

Referring to FIG. 3c the means forming kernel function filter 314 comprises opaque spatial filter wheel 324 having appropriately shaped "positive" and "negative" apertures 326 and 328 spaced at equal angular positions about the circumference of wheel 324. The shape of the area of apertures 326 corresponds to the central positive portion of the kernel function shown in FIG. 2, while the shape of the area of apertures 328 corresponds to the negative end portions of the kernel function shown in FIG. 2. Apertures 326 and 328 alternate with each other, with some opaque spacing separating them.

When wheel 324 is mounted for rotation about its center axis 330, scan-control means (not shown in the drawings) rotates wheel 324 in synchronous relationship with the mechanical scan of mask 304 (when this is intermittent) and the electronic scan of detector elements 302 of detector linear array 300 (discussed in more detail below). Further, as indicated in FIG. 3c the electronic scan axis of the array is arranged not to intersect the axis at rotation 330 at the wheel. Therefore, as wheel 324 rotates in a clockwise direction (as shown by the arrow in FIG. 3c), aperture 326 moves upwards towards filter 312, so that the top of rotating aperture 326 first comes into cooperative relationship with light passing through the bottom of filter 312. As wheel 324 further rotates, each portion (from top to bottom) of rotating aperture 326 successively comes into cooperative relationship with every portion (from bottom to top) of the light passing through linear Gaussian filter 312. Further because the electronic scan axis is situated above the axis of rotation 330, aperture 326 is oriented at an oblique angle with respect to filter 312 as it passes by filter 312.

The following description of the operation of the optical processing means shown in FIGS. 3a and 3b assumes that kernel function filter is in the form of the aperture wheel shown in FIG. 3c. In this case, if shadow mask 304 moves in its scan direction in small successive scan steps, each successive scan step will take place after each pair of both positive and negative apertures 326 and 328 have completed their rotation past filter 312. The size of each scan step is sufficiently small so that the light detected by array 300 for successive steps corresponds with overlapping spatial stripes of the two-dimensional spatial light field of shadow mask 304. Further, steerout means 322 is operated electronically to read out at high speed the accumulated photoelectric charge of each detector element 302 of array 300 immediately following the rotation of an aperture 326 or 328 completely past filter 312, at which time all the light through filter 312 is completely blocked by an opaque portion of wheel 324 situated between adjacent apertures 326 and 328. While the readout of detector elements 302 could be done in parallel, it is normally accomplished serially by an electronic scan of detector elements 302 of array 300.

The quantity of light flux at any point, such as point $P_1$, of the two-dimensional spatial field, which illuminates respective ones of detector elements 302 of array 300 is affected by the presence of both transmission filters 312 and 314. Further, as indicated in FIG. 3a, light originating at a single point $P_1$ does not illuminate only a single one of photodetectors 302, but in spread over a length $L_1$ that covers an entire subset of contiguous detector elements 302 of array 300. The number of contiguous detector elements 302 is a subset is determined by the width of a single detector element and the selected value of the distance d between image plane 310 and the surface of array 300. Since an object and its image bear a reciprocal relationship in optics, each individual detector element 302 is simultaneously illuminated with light from an entire subset of contiguous points of the two-dimensional spatial field of shadow mask 304. Thus, while the spatial field of light originating at respective closely-spaced points $P_1$ and $P_2$ are imaged at distinct points $P_1'$ and $P_2'$ in image plane 310, a whole subset of detector elements 302 are illuminated by a portion of the light diverging from image point $P_1'$ are also simultaneously illuminated with a portion of the light diverging from image point $P_2'$. Therefore, each detector element 302 corresponds with all points of an entire segment of given length of the two-dimensional spatial field (with the value of this given length being determined by the imaging optics, the width of each detector element 302 and the selected value of the distance d).

The accumulated photoelectric charge produced by each detector element 302 between successive electronic scans is proportional to the total light exposure it has received. In the arrangement shown in FIGS. 3a and 3b, the light exposure received by each individual detector element 302 consists of the convolution of a particular segment of the two-dimensional spatial field (that corresponds to that detector element 302) with a particular kernel function (i.e., that produced by aperture 326 or that produced by aperture 328 in conjunction with Gaussian filter 312.) Further, segments corresponding to adjacent ones of detector elements 302 inherently overlap. The given length of a segment (determined in accordance with the selected value of the distance d) is always made large relative to the wavelength of the high spatial frequencies of the regular periodic apertures of shadow mask 304 in the linear array plane (shown in FIG. 3a). Thus these high spatial frequencies in the linear array plane are integrated out.

In the plane perpendicular to the linear array plane, (shown in FIG. 3b), the total light exposure over the relatively long effective length of each detector element 302 corresponds to the convolution of the light passing through both Gaussian filter 312 and kernel function filter 314 (in the manner described aobve in connection with FIG. 3c). Specifically, linear Gaussian filter 312 has characteristics which is designed to operate as a low-pass spatial filter for removing high spatial frequencies (such as those due to the apertures of mask 304 in the mask scanned direction). Narrow Gaussian characteristics (i.e., a width of about 1.7 periods of the regular array apertures of mask 104) guarantees the smoothing of this intrinsic mask aperture periodicity.

The combination of the kernel function filter and the Gaussian filter, as described, is one way of producing a net effect in which both functions are successively convolved with the field function. The same effect could be produced also by designing the kernel function to include this first condition with the Gaussian function or in any other way which gives a reliably sharp cut-off of high spatial frequency components. It is to be understood, therefore, that although the double filter arrangement may be a convenience in relaxing requirements in filter design, it is not an essential part of the present method of removing high spatial frequency components.

As an alternative to the kernel function filter arrangement shown in FIG. 3c, kernel function filter 314 may comprise each of two graded optical filters 330 (such as the one shown in FIG. 3d), corresponding respectively to the positive portion and the negative portion of the kernel function shown in FIG. 2. In this case, switch means (not shown), operating in synchronous relationship with the scan of mask 304 and the steerout of detector array 300, alternately place each one of these two graded optical filters 330 in the relative position, with respect to Gaussian filter 312 and each detector element 302, shown in FIG. 3e. Specifically, the linear kernel function characteristic of graded optical filter 330 is oriented at an oblique angle with respect to Gaussian characteristic of filter 312, such that a convolution of light along the length of each detector element 302 takes place in a manner corresponding to that described above in connection with the use of a kernel function filter 314 in the form shown in FIG. 3c.

Steerout means 322 can electronically scan all the detector elements of array 300 at high speed. As described, two successive electronic scans (one for the "positive" portion of the kernel function and another for the "negative" portion of the kernel function) are required for each scan step of mask 300 in its scan direction. Even if a scan of mask 304 requires 500 scan steps (or a total of 1000 electronic scans of detector linear array 300), an entire shadow mask can be examined in a much shorter time than that required by any of the embodiments disclosed in the aforesaid related patent application Ser. No. 110,243 (RCA 73,388). Further, the selected value of d may be easily varied by adjusting either the relative position of imaging lens 308 and/or by varying its effective focal length. By suitably varying the selected value of d, a plurality of kernel functions, each corresponding to a different contiguous octave of spatial frequencies is achieved.

By way of example, imaging lens 308 in FIG. 3a may have a focal length of 2 cm and the kernel filter may have a total width of 7 mm in the direction of the linear array 300. The linear array 300 may comprise 400 detector elements, each having a width of 30 $\mu$m. In this case, a selected distance d of 400 $\mu$m provides a kernel function, of the type shown in FIG. 2, corresponding to a spatial frequency octave for shadow mask 304 of 4 cycles per degree (at the pupil of the eye of an observer of shadow mask 304 situated at a normal viewing distance from shadow mask 304). If wheel 324, in FIG. 3c rotates at 10 rps, an exposure time of about 10 milliseconds is provided for detector linear array 300 between successive electronic scans thereof. In order to avoid shot noise in the detector elements with this exposure time, an illumination of about 1000 foot lamberts is desirable.

Figures 3D, 3E:
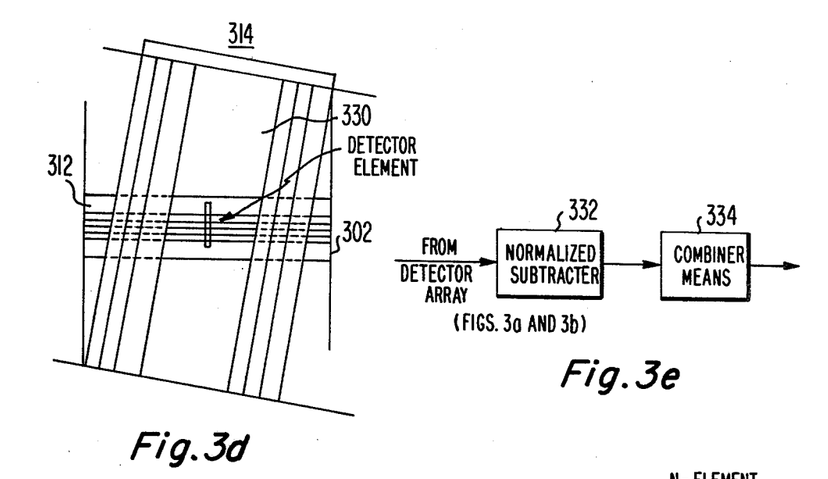

Each electronic scan of array 300 by steerout means 322 produces a serial output which is applied as an input to normalized subtractor 332 of the electronic processing means of the first embodiment of the present invention, shown in FIG. 3e. The purpose of normalized subtractor 332 is to subtract the negative kernel function convolved output of each particular detector element of array 300 from the positive kernel function convolved output of that particular detector element of array 300. It is essential that the effective gain of the overall system for deriving the positive kernel function convolutions be substantially equal to that for deriving the negative kernel function convolutions, so as to eliminate the DC (constant) component of the data. Therefore, normalized subtractor 332 includes means for normalizing the respective gains of the outputs fo the positive and negative kernel function convolutions before making an individual subtraction for each detector element of the array. By way of example, normalized subtractor 332 may include a first memory for storing samples of the respective outputs from each detector element of the array for the positive kernel function convolutions and a similar second memory for the negative convolution memories. By comparing the sum of all the sample values of the second memory to the sum of all the sample values of the first memory, a scaling factor may be determined for normalizing the respective sample values of the positive and negative kernel function convolutions before making each of the individual subtractions. The successive outputs for normalized subtractor 332 may then be applied as inputs to combiner means 334, which is the type discussed above in connection with electronic processing means 104 of the FIG. 1. The output of combiner 334 may, in itself, be the "visibility figure" output of FIG. 1, or, alternatively, the output of combiner 334 may be applied to further components of electronic processing means of 104 from which the visibility figure output is ultimately derived.

Although, as so far described, the optical processing means shown in FIGS. 3a and 3b involves one-dimensional transforms, it should be understood that two-dimensional transforms may be achieved by employing kernel functions with circular or other two-dimensional symmetry, in a manner analogous to that disclosed in the aforesaid related patent application Ser. No. 110,243 (RCA 73,388).

Figure 4A:
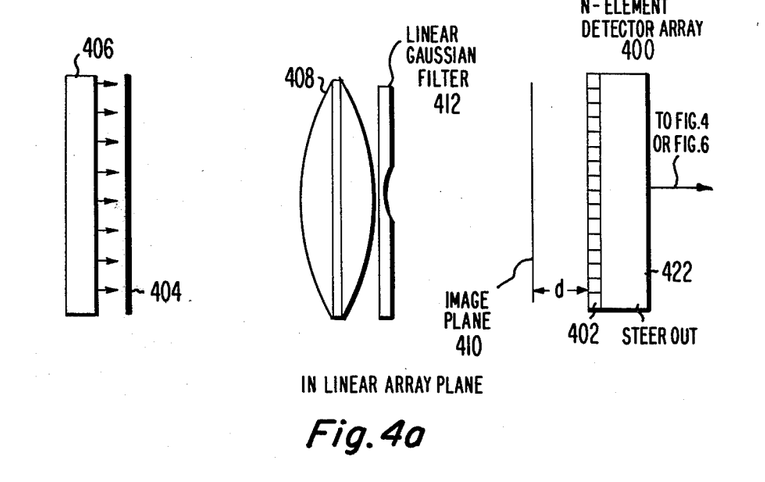
FIGS. 4a and 4b illustrate optical processing means employed by each of second and third embodiments of the present invention.
Figure 4B:
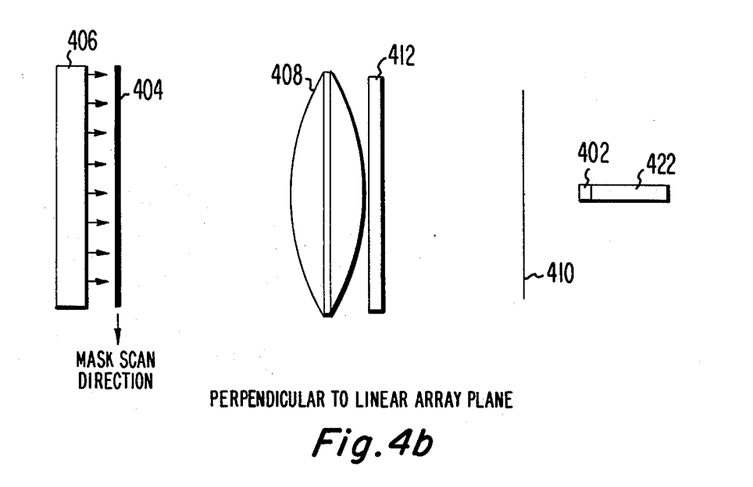

The second and third embodiments of the present invention differ from the first embodiment thereof, described above, in two significant respects. First, convolution of spatial segments of the two-dimensional spatial field with a given kernel function is accomplished electronically in the second and third embodiments (i.e., after detection), rather than optically (before detection). Second, the orientation of these convoluted segments in the second and third embodiments is parallel to the mechanical mask scan direction, rather than being parallel to the detector array. FIGS. 4a and 4b illustrate the optical processing means employed by each of the second and third embodiments of the present invention. In FIGS. 4a and 4b, items 404, 406, 408 and 410 are identical in all respects to the corresponding items 304, 306, 308 and 310 of FIGS. 3a and 3b. However, the detector elements 402 of N-element detector array 400, in FIGS. 4a and 4b, have a smaller length perpendicular to the linear array plane than do corresponding detector elements 302 of array 300 of FIGS. 3a and 3b. Further, the orientation of linear Gaussian filter 412 in FIGS. 4a and 4b is rotated 90° with respect to that of corresponding linear Gaussian filter 312 of FIGS. 3a and 3b. In addition, the optical processing means shown in FIGS. 4a and 4b contains no items corresponding to kernel function filter 314, image plane aperture spatial filter 318 and cylindrical lens 320 of FIGS. 3a and 3b.

In the arrangement shown in FIGS. 4a and 4b, the presence of linear Gaussian filter 412, together with the displacement of the surface of detector array 400 from image plane 410 by a distance d, insures that undesired high spatial frequencies, such as those due to the periodicity of the apertures of shadow mask 404, are filtered out from the light impinging on the surface of detector elements 402 of array 400. These frequencies are above half the sampling frequency and would thus introduce serious aliasing if not filtered out. However, components of the non-uniformities in the two-dimensional spatial field from shadow mask 404, which are within the frequency band detected by the eye remain in the light detected by the elements of array 400.

At the end of each mechanical scan step of mask 404, N-element detector array 400 is electronically scanned to produce a serial analog output signal. In the case of the second embodiment of the present invention, this serial analog output signal is applied to the electronic processing means shown in FIG. 5, and in the case of the third embodiment of the present invention, this serial analog output signal is applied to the electronic processing means shown in FIG. 6.

Figure 5:
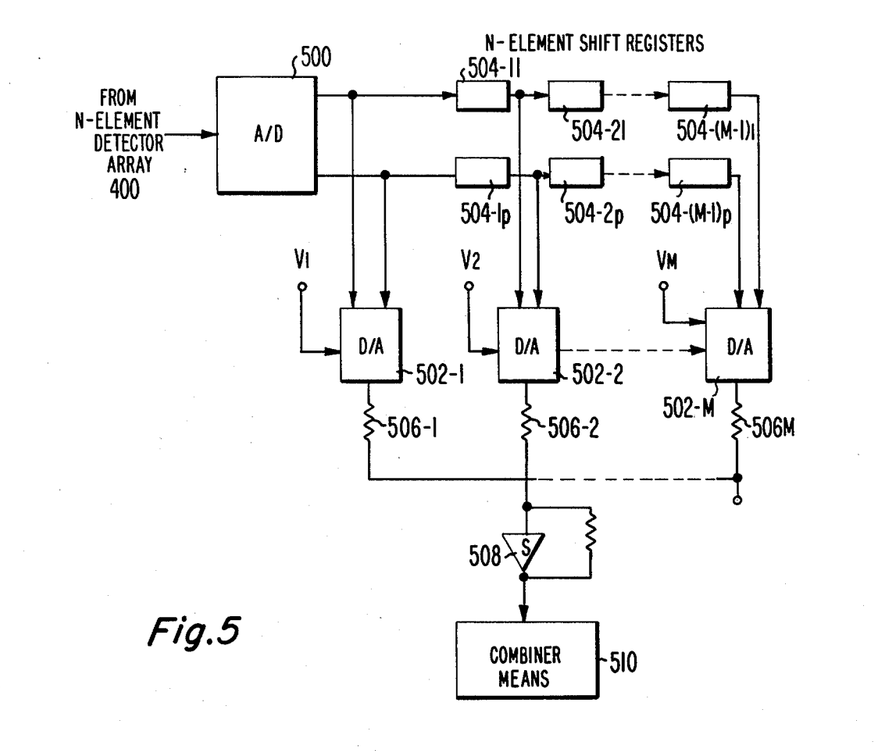
FIG. 5 illustrates electronic processing means employed by the second embodiment of the present invention.

Referring to FIG. 5, the serial analog output signal from N-element detector array 400 is applied as an input to analog-to-digital converter 500. In response to an electronic scan of detector elements 402, analog-to-digital converter 500 successively samples the level of the output from each individual detector element 402 and converts this level into a p-bit digital value. The output from analog-to-digital converter 500 is directly applied as an input to digital-to-analog converter 502-1, which has a reference voltage $V_1$ applied as an input thereto. In addition, the output from analog-to-digital converter 500 is applied as an input to a first set of p N-element shift registers 504-11 . . . 504-1p. The output from this first set of N-element shift registers is directly applied as an input to a second digital-to-analog converter 502-2, which has a reference voltage $V_2$ applied an input thereto. The output from the first set of N-element shift registers also is applied as an input to a second set of p N-element shift registers 502-21 . . . 504-2p. Altogether there are (M-1) sets of N-element shift registers. In a manner similar to that described above for the first set of N-element shift registers, the respective outputs from the second . . . (M-2) sets of N-element shift registers are applied as inputs to the third . . . (M-1) sets of p N-element shift registers, as indicated in FIG. 5. Further, the output of each of the third . . . (M-1)th set of N-element shift registers is directly applied as an input to a corresponding one of digital-to-analog converters 502-3 . . . 502-M, each of which has a corresponding reference voltage $V_3$ . . . $V_M$ applied as an input thereto. Thus, as shown in FIG. 5, the output from the (M-1)th set of p N-element shift registers 504-(M-1) . . . 504-(M-1)p is applied as an input to digital-to-analog converter 502-M, which has a reference voltage $V_M$ applied as an input thereto.

The respective outputs of digital-to-analog converters 502-1 . . . 502-M are applied through their respective output resistances 506-1 . . . 506-M as a common input to summing amplifier 508. The output from summing amplifier 508 is applied as an input to combiner 510, which corresponds in function to combiner 334 of FIG. 3e.

The combination of the values of reference voltages $V_1$ . . . $V_M$ and the output resistances 506-1 . . . 506-M correspond to equally spaced sample values of the given kernel function shown in FIG. 2. In practice, M should have a value of at least 6, to give a sufficiently accurate transform.

Since there are N-elements in each shift register, at any instant of time, the outputs from and the input to each of the (M-1) sets of registers originates from the same single one of the N detector elements 302 of array 400. However, each of the (M-1) sets of shift registers introduces a delay.

Thus, in response to the electronic scan of array 400 by steerout means 422 for the Mth scan step, the output from summing amplifier 508 sequentially corresponds to the convolution by any particular one of detector elements 402, in turn, of a field function corresponding to data points, for that particular detector element 402, of mask scan steps 1 . . . M (in the case of a higher spatial-frequency octave) with the given kernel function defined by reference voltages $V_1$ . . . $V_M$ and resistors 506-1 to 506-M. Similarly, during the (M+1) scan step, the sequential convolutions for each of the detector elements 402 of linear array 400 correspond to mask scan steps 2 . . . (M+1). This process is repeated for each additional scan step, until the entire area of the shadow mask has been scanned. In the case of kernel functions with lower center frequency, M will be proportionally larger. The center frequency will be determined by the product of M and the mechanical scan speed.

In the embodiment shown in FIG. 5, the number of required bits, p, must be relatively large, so that a slight variation in the brightness of the illumination of array 400, corresponding to small-amplitude nonuniformities in mask 404, is not lost. This means that in the embodiment shown in FIG. 5, the total number of N-element shift registers that are required is very large, typically about 400. This number may be reduced by a subtractive system, as shown in FIG. 6.

Figure 6:
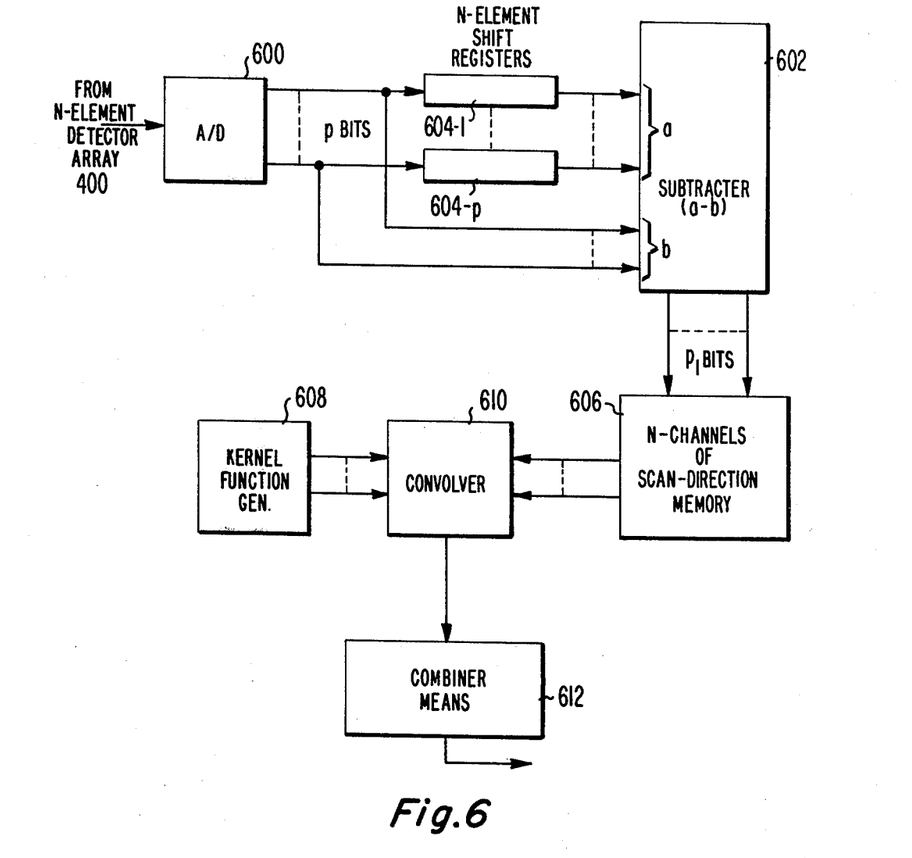
FIG. 6 illustrates electronic processing means employed by the third embodiment of the present invention.

Referring to FIG. 6, analog-to-digital converter 600, which has a serial analog input from N-element detector array 400 applied thereto and which is structurally and functionally identical to analog-to-digital converter 500 of FIG. 5, derives a p-bit output signal manifesting the digital value of the light exposure level at each individual detector element 402 of array 400 during each electronic scan thereof. The p-bits are directly applied as input b to subtracter 602 are also applied as inputs to a single set of p N-element shift registers 604-1 . . . 604-p. The output from the single set of shift registers is applied as input a to subtracter 602. Subtracter 602 derives a digital-valued output signal, having $p_1$ bits, corresponding to the difference between the digital values of a and b.

The digital value b corresponds with the level of light exposure of each individual particular detector element 402 during a current scan step of mask 404. Similarly, the digital value a corresponds with the light exposure of each corresponding particular one of detector elements 402 during the prior scan step. Since both the a input and the b input are comprised of a relatively large DC (constant) component, and only a relatively small variable component, the digital value of the difference signal output from subtracter 602 is much smaller than that of either a or b. Therefore, the difference signal output from subtracter 602 may be comprised of only $p_1$ bits (where $p_1$ is significantly smaller than p).

The output from subtracter 602 is applied to N-channels of scan-direction memory 606, this memory being similar to that shown as shift registers 504 in FIG. 5.

Memory 606 may be organized into rows and columns with each column corresponding to a separate one of the N channels and each row corresponding to the difference between two successive complete electronic scans of the set of N-element shift registers. During each complete cycle of the set of shift registers, respective outputs from subtracter 602 fill up one row of memory. The capacity of memory 606 is sufficient to store all the outputs produced by subtracter 602 during one complete scan of the area of mask 404.

Each column of memory 606 comprises a plurality of uniformly-spaced segments, each corresponding to a given length in the mask scan direction. This given length is greater than the uniform-spacing, so that successive segments overlap. During readout of memory 606, the successive segments of each of the N columns, in turn, are sequentially convolved with an appropriate kernel function from kernel function generator 608 in convolver 610.

Figure 6A:
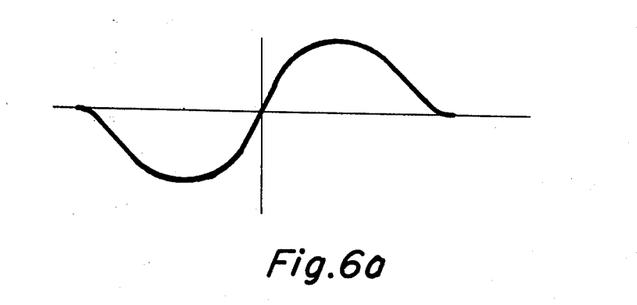
FIG. 6a is a graph of a given kernel function suitable for use for the third embodiment of the present invention.

Because the information generated by subtracter 602 is neither a nor b, but is the difference between a and b, the required kernel function generated by generator 608 is not the waveform shown in FIG. 2, but, instead, is the integral of the waveform shown in FIG. 2. The waveform for this integral is shown in FIG. 6a.

The sequential convolutions from each of the segments of each of the N columns, in turn, are applied as successive inputs to combiner 612, which performs the same function as combiner 334 of FIG. 3e.

What is claimed is:

1. In an apparatus comprising signal processing means including detector means for sequentially convolving, with a given kernel function, the intensity values in each of uniformly-spaced segments aligned with a certain dimension of a two-dimensional spatial field of intensities, wherein said field is derived from an illuminated two-dimensional object that is scanned in a certain direction with respect to said detector means, each segment having a given length along said certain dimension that is greater than said uniform spacing and said given kernel function being characterized by (1) having a limited spatial extent along said certain dimension corresponding to said given length, (2) having an integrated value over its limited spatial extent substantially equal to zero and (3) exhibiting a limited spatial frequency passband, and wherein said field may include certain spatial frequencies substantially higher than the upper limit of the limited spatial frequency passband of said given kernel function, the improvement:
    wherein said detector means comprises a linear array of contiguous detector elements oriented along given line of a given plane spaced from said object, said given line being in substantially skew relationship with said certain scan direction of said object,
    wherein said signal processing means comprises optical processing means including an imaging lens and a linear Gaussian spatial filter oriented substantially perpendicular to said certain dimension of said field for imaging said object on an image plane displaced a selected distance, whereby each detector element is simultaneously illuminated by light originating from an extended linear region of said field, the length of said extended region being determined by the size of said selected distance, said optical processing means as a whole exhibiting a low spatial frequency passband that includes the limited passband of said kernel function but rejects said certain higher spatial frequencies of said field, whereby said certain high spatial frequencies are removed from the illumination of said array of detector elements, and
    wherein said signal processing means further comprises electronic processing means including steerout means for deriving successive outputs from each of the respective detector elements of said array.

2. The apparatus defined in claim 1, wherein the projection of said certain scan direction on said given plane is substantially perpendicular to said given line.

3. The apparatus defined in claim 2, wherein said certain dimension is substantially parallel to said given line and perpendicular to said certain scan direction, and wherein each separate one of said segments of given length coincides with the extended linear region illuminating a different one of said detector elements.

4. The apparatus as defined in claim 3, wherein said optical processing means further include kernel-function spatial filter means oriented in such cooperative spatial relationship with respect to said imaging lens and said Gaussian filter as to expose each detector element of said array with illumination that comprises the convolution of that segment of said field corresponding to the detector element with said given kernel function.

5. The apparatus defined in claim 4,
    wherein said objec is scanned in said scan direction in a plurality of successive overlapping scan steps,
    wherein said kernel-function spatial filter means comprises separate spatial filters corresponding respectively to the positive spatial portions and to the negative spatial portions of said given kernel function, each of said positive and negative filters being individually placed successively into cooperative spatial relationship with said imaging lens and said Gaussian filter during each single one of said scan steps,
    wherein said steerout means is operated during each single one of said scan steps both for said positive filter and for said negative filter, and
    wherein said electronic processing means includes a normalized subtracter coupled to said steerout means for subtracting the output from each detector element of said array for said negative filter from the output from that detector element for said positive filter.

6. The apparatus defined in claim 5, wherein the effective length in said given plane of each detector element perpendicular to said given line is large relative to the width of detector element along said given line, and
    wherein each of said positive and negative filters, when placed into cooperative spatial relationship with said Gaussian filter, is disposed with their axes in an oblique direction with respect to the effective length of each detector element, this length being perpendicular to the axis of the Gaussian filter,
    whereby each detector element is exposed to illumination that comprises the successive convolution of the segment of said field corresponding to the detector element with the Gaussian filter characteristic and then with said given kernel function.

7. The apparatus defined in claim 6, wherein said kernel function spatial function means comprises a relatively-large opaque rotatable wheel with its axis parallel to the optic axis of the system, said wheel having a plurality of transparent apertures disposed at equiangular positions about the circumference thereof with adjacent apertures being separated by opaque portions of said wheel, alternate ones of said apertures having shaped area corresponding to the positive portions of said given kernel function and the remaining one of said apertures having spaced areas corresponding to the negative portions of said given kernel function, said wheel being disposed with respect to said Gaussian filter such that as said wheel rotates each transparent aperture, in turn, moves past said linear Gaussian filter to thereby expose said detector elements with illumination that has passed through both said Gaussian filter and that transparent aperture then moving therepast.

8. The apparatus defined in claim 6, wherein both said positive and said negative filters are graded optical transmission filters.

9. The apparatus defined in claim 5, wherein said Gaussian filter is a graded optical transmission filter.

10. The apparatus defined in claim 2, wherein said certain dimension is substantially perpendicular to said given line and parallel to said certain mechanical scan direction, and whereby each separate one of said segments of given length is perpendicular to the extended linear region illuminating a different one of said detector elements.

11. The apparatus defined in claim 10, wherein said object is scanned in said scan direction in a plurality of successive scan steps, and wherein said electronic processing means comprises,
an analog-to-digital (A/D) converter for converting the level of an analog signal applied as an input thereto into a p-bit digital-valued signal,
a series of M digital-to-analog (D/A) converters each of which derives an analog output having a level proportional to the product of a p-bit digital valued signal and the level of a reference signal applied as inputs to that D/A converter, the respective levels of the reference signals applied to each of said series of D/A converters 1 . . . M corresponding to equally spaced sample points of said given kernel function,
summing means for summing the respective analog outputs of all M of said D/A converters,
(M-1) sets of shift registers, each set being comprised of p shift registers with each shift register comprised of the same number of elements as the number of detector elements in said array, means coupling corresponding ones of the shift registers of all M sets in series,
means applying the p-bit digital-valued signal from the A/D converter as an input to a first of said M D/A converters and as an input to the corresponding p shift registers of the first set of said serially-coupled (M-1) sets of shift registers,
means for respectively applying p-bit digital-valued signal outputs from the respective serially-coupled sets of shift registers 1 . . . (M-1) to the respective series of D/A converters 2 . . . M, and
means coupling said steerout means to said A/D converter for serially applying the outputs from every detector element of said array for each of certain scan steps as analog inputs to said A/D converter.

12. The apparatus defined in claim 11, wherein said certain scan steps comprise each and every scan step.

13. The apparatus defined in claim 11, wherein said certain scan steps comprise a predetermined fraction of all said scan steps.

14. The apparatus defined in claim 10, wherein said object is scanned in said scan direction in a plurality of successive scan steps, and wherein said electronic processing means comprises:
an analog-to-digital (A/D) converter for converting the level of an analog signal applied as an input thereto into a p-bit digital-valued signal,
a set of p shift registers each of which is comprised of the same number of elements as the number of detector elements in said array,
a subtractor for deriving a $p_1$-bit digital-valued output therefrom corresponding to the difference between the respective digital values of first and second p-bit inputs thereto, where $p_1$ is smaller than p,
means for applying the p-bit digital-valued signal from said A/D converter as an input to said set of shift registers and as said first input to said subtracter means,
means for applying the p-bit digital-valued output from said set of shift registers as the second input to said subtracter means, and
means coupling said steerout means to said A/D converter for serially applying the outputs from every detector element of said array for each of certain scan steps as analog inputs to said A/D converter.

15. The apparatus defined in claim 4,
wherein said electronic processing means further includes a memory for separately storing the respective $p_1$-bit digital-valued outputs from said subtracter derived in response to all of said outputs from every detector element of said array for each of said certain scan steps, and a convolver, coupled to said memory and responsive to said stored $p_1$-bit digital values, for sequentially convolving each of a plurality of overlapping uniformly-spaced segments, each segment corresponding to a given length in said scan direction of the portion of said field detected by an individual one, of said detector elements, with a modified kernel function which is the integral of said given kernel function.

16. The apparatus defined in claim 15,
wherein said convolver comprises means for serially performing said sequential convolutions for each of said respective detector elements of said array in succession.

17. The apparatus defined in claim 15,
wherein said convolver comprises means for simultaneously performing said sequential convolutions for each of said respective detector elements in parallel.

18. The apparatus defined in claim 15, wherein said certain scan steps comprise each and every scan step.

19. The apparatus defined in claim 15, wherein said certain scan steps comprise a predetermined fraction of all said scan steps.

* * * * *

UNITED STATES PATENT AND TRADEMARK OFFICE
CERTIFICATE OF CORRECTION

PATENT NO. : 4,282,510

DATED : August 4, 1981

INVENTOR(S) : Peter David Southgate

It is certified that error appears in the above-identified patent and that said Letters Patent is hereby corrected as shown below:

Column 2, line 21, "meens" should be ---means---
Column 3, line 11, "accomplishd" should be ---accomplished---
Column 3, line 50, "(2πfx/3" should be ---(2πfx)/3---
Column 4, line 10, "orineted" should be ---oriented---
Column 4, line 43, "directin" should be ---direction---
Column 6, line 58, "aobve" should be ---above---
Column 8, line 13, "fo" should be ---for---
Column 10, line 6, "outputs" should be ---output---
Column 10, lines 19 and 20, "$V_M$ and resistors 506-1 to 506-M. Similarly, during the (M + 1)" should not be in italics;
column 10, line 49, "a" should be "$\underline{a}$".

Column 10, line 52, "a and b" should be ---$\underline{a}$ and $\underline{b}$---
Column 10, line 53, "b" should be ---$\underline{b}$---

UNITED STATES PATENT AND TRADEMARK OFFICE
CERTIFICATE OF CORRECTION

PATENT NO. : 4,282,510

DATED : August 4, 1981

INVENTOR(S) : Peter David Southgate

It is certified that error appears in the above-identified patent and that said Letters Patent is hereby corrected as shown below:

Column 10, line 56, "a" should be ---$\underline{a}$---
Column 10, line 58, "a" should be ---$\underline{a}$---
Column 10, line 59, "b" should be ---$\underline{b}$---
Column 10, line 63, "a or b" should be ---$\underline{a}$ or $\underline{b}$---
Column 11, line 21, "a nor b" should be ---$\underline{a}$ nor $\underline{b}$---
Column 11, line 21, "a and b" should be ---$\underline{a}$ and $\underline{b}$---.

Signed and Sealed this

Eighth Day of December 1981

[SEAL]

Attest:

Attesting Officer

GERALD J. MOSSINGHOFF

Commissioner of Patents and Trademarks